United States Patent [19]

Newton

[11] 4,329,787
[45] May 18, 1982

[54] DROPLET EXPLODING AND FREEZING APPARATUS AND METHOD

[76] Inventor: William A. Newton, P.O. Box 161633, Miami, Fla. 33116

[21] Appl. No.: 258,391

[22] Filed: Apr. 28, 1981

Related U.S. Application Data

[63] Continuation-in-part of Ser. No. 109,666, Jan. 4, 1980, abandoned.

[51] Int. Cl.³ .......................... F26B 3/34; F26B 5/06; F26B 13/30
[52] U.S. Cl. ............................................ 34/1; 34/5; 34/92
[58] Field of Search ...................... 34/1, 5, 92; 62/74, 62/374

[56] References Cited

U.S. PATENT DOCUMENTS

| | | |
|---|---|---|
| 3,011,543 | 12/1961 | McCormick, Jr. .................... 34/1 |
| 3,228,838 | 1/1966 | Rinfret et al. ....................... 34/5 |
| 3,416,153 | 12/1968 | Hertz et al. ......................... 346/15 |
| 3,710,933 | 1/1973 | Fulwyler et al. ..................... 209/3 |
| 3,932,943 | 1/1976 | Briggs et al. ........................ 34/5 |

Primary Examiner—John J. Camby
Attorney, Agent, or Firm—William A. Newton

[57] ABSTRACT

Disclosed is an apparatus and method for freezing and preserving in a viable state microorganisms wherein droplets are formed from an aqueous solution having suspended therein the microorganisms, the droplets are exploded into a plurality of smaller droplets by applying an electrical force which counteracts the surface tension of the droplets, and the microorganisms, with a substantial portion of the solution removed therefrom, are frozen in a moving bath of liquid refrigerant. The frozen droplets are thawed or alternatively dried by sublimation.

6 Claims, 1 Drawing Figure

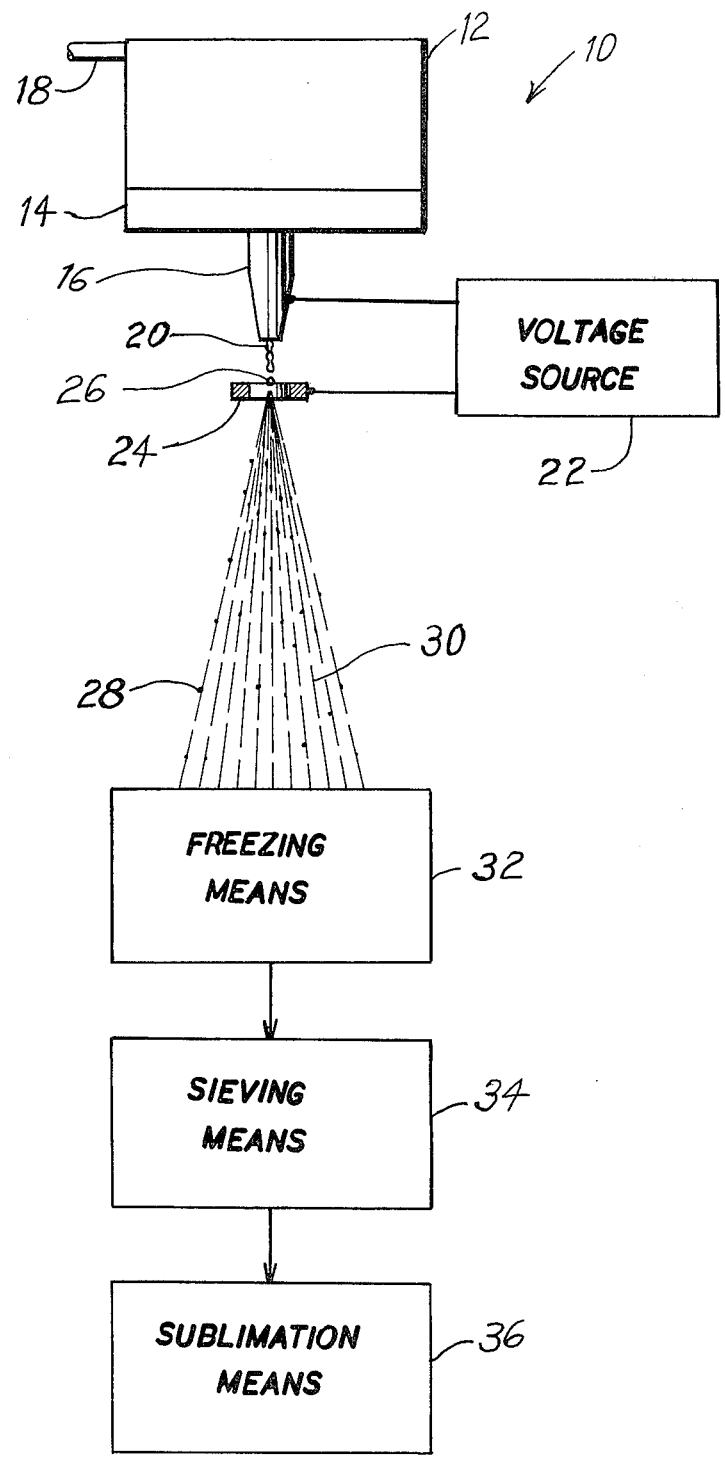

DROPLET EXPLODING AND FREEZING APPARATUS AND METHOD

This application is a continuation-in-part of application Ser. No. 109,666, filed Jan. 4, 1980, now abandoned.

FIELD OF THE INVENTION

The present invention relates to an apparatus and method of preserving viable biological cells through freezing.

DESCRIPTION OF THE PRIOR ART

Biological cells at temperatures just below the freezing point of its internal constituents are especially liable to injury, both from ice crystal growth and from increasing solute concentrations. If freezing is carried out slowly, extracellular ice crystals are formed, which cause water to be drawn from the cells, leading to a certain degree of cell plasmolysis and causes considerable deformation of the cells. If more rapid freezing is undertaken, small ice crystals are formed within the cells, and they can be at least as lethal as the extra cellular crystals. However, if ultrarapid freezing is undertaken, then ice crystal formation can be avoided and, assuming rapid enough thawing, some cells can be frozen and thawed without injury.

Rapid freezing requires a rapid cooling rate, the cooling rate being dependent upon the sample's size, shape, and thermal properties; on the velocity of immersion, and on the temperature and physical properties of the coolant. Moreover, ice crystals, as they grow, release latent heat of crystallization; hence, the size and number of ice crystals can slow the rate of cooling.

As shown in U.S. Pat. No. 3,228,838 to Rinfret et al., the cooling rate of cells can be greatly increased by forming a plurality of liquid droplets, having the cells suspended therein, and then spraying the droplets into a stream of liquid nitrogen. Hence, the sample is substantially reduced in size and given a spherical contour. Generally, droplets ranging from 1 to 0.5 millimeters have been formed. This allows cooling rates that are fairly fast, for example, a 0.5 millimeter droplet freezes in about 2 seconds. In freezing droplets containing viable biological cells or like microorganisms, with the intent of preserving the viability of the cells, it has been found that the inert liquid refrigerant must have a temperature substantially below the critical temperature zone of the cell. The critical temperature zone of a biological cell is the temperature range, beginning at the freezing point of the cell, through which the rate of cooling must be rapid enough to limit the time available for degradative processes to occur in the cell. Despite these relatively fast cooling rates of the droplets, only red blood cells have any substantial survival rate when frozen in this manner. One of the primary problems with this procedure is that the solution of the droplet, which encompasses the cells, still provides a substantial thermal barrier to rapid and uniform rates of cooling. As far as uniform cooling rates are concerned, it has been shown that with droplets of this size, the cells in the inner region will lose heat at substantially different rates than cells in peripheral regions. Hence, the thermal conditions prevailing during cooling require that the cells be capable of withstanding a rather broad range of heat removal rates. Only red blood cells or erythrocytes have withstood these variations. Even so, it has been estimated that, with red cell recovery in 1 millimeter droplets as a reference standard, there has been roughly a 2% decline in recovery for each millimeter of increased sample thickness. As to the overall rate of cooling, this is more specifically related to the size and geometry of the sample, the temperature differentials, and the various coefficients of heat transfer involved. Since aqueous systems are relatively poor conductors of heat, the solution surrounding the cells creates a temperature gradient between the liquid refrigerant and the cells, which slows the rate of cooling. Moreover, as the surrounding solution freezes, the thermal conductivity and specific heat of the ice will be even more of a hinderance to the rate of cooling. In summary, the greater the cross section of the sample, the slower the overall rate of heat transfer and the longer the time period that the cell will stay in the critical temperature zone. Many of the same problems exist during thawing, with the exception that there is no problem with an insulating gas film being formed, as occurs during cooling when the droplet enters the liquid nitrogen.

The size of the droplets in the prior art arrangements, such as those shown in the above mentioned U.S. Pat. Nos. 3,228,838 to Rinfret et al. and 3,932,943 to Briggs et al., can be only made relatively large, so that the vast majority of the droplet comprises the liquid surrounding the cells. For example, 10 micron diameter cells might be found in a 500 micron diameter droplet. If the orifice of the nozzle producing the droplets is made too small, the cell structure will be disrupted during fluid flow so as to kill the cell. Hence, there are inherent limitations on making droplets having smaller diameters by having smaller nozzle orifices. Therefore, although the prior art practice of forming droplets provides for smaller cross-sectional dimensions to the sample there is a need for improvement when the preservation of cells and like microorganisms is attempted.

Another important factor in preserving viable cells is the regulation of the temperature in the course of thawing, or alternatively, drying by sublimation. Thawing and drying represent alternative pathways by which cells can be returned from the frozen state. Both situations create problems with recrystallization. More specifically, it has been shown that crystals begin to form in pure amorphous ice if the temperature rises to $-130°$ C. The formation of ice crystals at these latter stages again causes the previously described cell damages. With thawing and drying, as with freezing, the rate of water removal is dependent upon the sample's cross-sectional dimensions.

At least one prior art scheme has attempted to dry the frozen droplets by sublimation in a vacuum. However, after drying, the cells, at some point, must be reconstituted. However, following drying, it has been found to be necessary to crush the dried droplets prior to reconstitution in order that resolvation be rapid. The sublimation of the droplet leaves the dried cell or cells surrounded with a crust of dried solutes, such as salt. Accordingly, in this freeze drying technique there is a need to substantially reduce the solution surrounding the cells prior to freezing. More generally, there is a need for decreasing the frozen liquid surrounding the cell in any process wherein the cell is frozen and subsequently sublimated and reconstituted. One prior art procedure for reducing the frozen solution content surrounding the cell comprises spreading the cells on a nylon gauze that hangs free in a vacuum chamber wherein freezing through evaporation and sublimation is conducted. The present invention teaches a different way of decreasing the surrounding liquid.

In freeze drying, it is known that viable cells can be overdried. When cells are randomly distributed through a large droplet of a diameter from 0.5 to 1 millimeter, its precise position in that droplet will effect the amount of water removed therefrom. Hence, there is a need for eliminating the random degree of drying.

Temperature regulation when drying by sublimation provides an added problem, in that the temperature must be sufficiently low to prevent any melting of the solution and sufficiently high to allow the sublimation process to be completed within a reasonable time. Hence, there is a need for even more uniform cooling throughout the cell when drying is involved.

In summary, the size of the droplets presently frozen in the prior art devices, when combined with the ease of which water crystallizes, the large heat of fusion to be removed, and the inherent slowness of aqueous heat conduction, conspire to make ultrarapid freezing for biological cells impractical, except for red blood cells. Accordingly, there is a need in the art for a way to reduce the sample being frozen to microscopic dimensions approaching those of the cells.

It is known in the art of cytology to apply a voltage to droplets having particles therein for charging the droplets, as shown by U.S. Pat. No. 3,710,933 to Fulwyler et al. However, the magnitude of the voltage falls short of that required for breaking up the droplets, as contemplated in the present invention. It is also known that ink droplets in an electric field can be exploded into a plurality of smaller droplets, as shown in U.S. Pat. No. 3,416,153 to Hertz et al.

SUMMARY OF THE INVENTION

The present invention is directed toward an improved apparatus and method for freezing and preserving microorganisms, such as biological cells, wherein the microorganisms are positioned inside liquid droplets of an aqueous solution and then frozen. The improvement comprises exploding the droplets by applying an electrical force thereto so as to form a plurality of droplets of smaller cross-sectional dimensions. Hence, at least a substantial portion of the aqueous solution of the droplet which previously surrounded a given microorganism is now removed from that microorganism. Consequently, the rate of cooling is increased which in turn reduces the time the cells remain in the critical temperature zone. Additionally, more uniformity of cooling of the droplets is provided, therefore narrowing the range of heat removal rates that the microorganism must withstand. This improvement of droplet exploding prior to freezing reduces ice crystal formation and solute concentrations which can result from freezing.

After the microorganisms have been frozen, they can be stored in their frozen state and thawed in a conventional manner when needed. Alternatively, the microorganisms can be dried by sublimation. In either case, the smaller cross-sectional dimensions of the frozen droplets having microorganisms provide for more rapid thawing or drying; thereby again minimizing the time that the microorganism is within the critical temperature zone. This reduces recrystallization of ice. Moreover, the improvement of the uniformity of heat transfer can help prevent overdrying of the microorganisms. Additionally, since the vast majority of the aqueous solution has been removed from the microorganism prior to freezing, a residual solute crust, which is deposited around the microorganism by the sublimation of ice during drying, is greatly reduced or substantially eliminated, thereby eliminating the need for removing a solute crust prior to reconstitution.

BRIEF DESCRIPTION OF THE DRAWING

Further objects and advantages of the present invention will become apparent as the following description proceeds, taken in conjunction with the accompanying drawings in which:

The sole FIGURE shows a partial sideview and partial schematic view of the freezing apparatus of the present invention.

DESCRIPTION OF THE PREFERRED EMBODIMENT

Referring to the sole FIGURE, a freezing apparatus 10 for microorganisms such as biological cells is shown having a pressurized container 12 with a saline solution or like aqueous solution of viable biological cells. The container 12 is connected through a filter 14 to a small diameter nozzle 16. The filter 14 limits the range of cell sizes that will pass on to the nozzle 16. The container 12 is provided with gas tube 18 which fluidly connects to a sterilized or clean air supply means (not shown) for providing a positive pressure to the container 12, when desired. A liquid jet 20, having the cells suspended therein, is ejected from the nozzle 16. A potential difference is impressed by a voltage source 22 between the nozzle 16, which is formed of metal, and an electrode 24, which is formed of metal and preferably has a ring-like configuration.

In a well known manner, the jet 20 is broken into droplets 26 soon after leaving the nozzle 16, due to the action of surface tension. The embodiment of the drawing takes advantage of the natural dynamic instability of cylindrical liquid jets. Whenever a jet is perturbed at a wavelength exceeding the initial jet circumference, the action of surface tension renders the jet unstable and leads to the production of droplets. As in the embodiment of the drawing, if the perturbation is created by friction or other random source, a plurality of unstable wavelengths will be present and will lead to the production of randomly sized and spaced droplets. As is known in the art, the pressure applied to the container 12 and the diameter size of the nozzle 16, can be adjusted to control the size and number of droplets 26. These factors and the dilution, if any, of the sample forming the liquid jet 20 can be adjusted to change the number of cells in each droplet. In practice, depending upon the intended purpose, each droplet 26 will contain many cells, with the operator of the apparatus 10 preferably adjusting the above factors to increase the number of cells per droplet until the cell concentration significantly reduces the number of small droplets 28 which are produced from the large droplets 26. The voltages and droplet sizes can vary over wide margins without impairing the operation of the apparatus 10; however, the minimum droplet size is primarily dependant upon the sizes of the microorganisms being processed. Preferably, with the above described apparatus, the droplet size should be no smaller than 250 microns in diameter for whole blood to avoid destruction of cells by mechanical forces involved in the formation of small droplets.

The electrode 24 is positioned near the point of the formation of droplets 26 and the droplets 26 are electrically charged by the electrode 24. As is known, if the potential difference is sufficiently large, each droplet will explode into a plurality of smaller droplets 28. This is due to the electric charge on the droplet creating an electric force greater in magnitude and opposite in direction to the surface tension force. Each of the exploded smaller droplets 28 have retained at least some of the original charge. Hence, the droplets 28 will repel each other and will form a spray 30, as shown and described in detail in U.S. Pat. No. 3,416,153 to Hertz et al. Generally, the greater the applied voltage difference, the more divergent the spray 30 becomes. Hence, the explosion of the droplet 26 removes most of or substantially all of the aqueous solution from the cells contained in the droplet.

As illustrated in the drawing, the trajectories of the droplets 28 are such that they are sprayed into a known freezing means 32 wherein the droplets 28 are intercepted by a moving bath of fluorocarbon refrigerant having a sufficiently low temperature to rapidly freeze the droplets 28. The specific structure of the freezing means 32 is per se not part of the invention and can comprise one of any of the numerous known arrangements, such as those illustrated in U.S. Pat. No. 3,228,838 to Rinfret et al. The frozen droplets are removed from the refrigerant by known sieving means 34, such as those shown in the above mentioned U.S. Pat. No. 3,228,838. As will be obvious to those skilled in the art, means of freezing the droplets 28, other than a liquid refrigerant, can be used with the droplet exploding technique of the present invention.

As has been previously described, biological cells must go through a "critical temperature zone" during which the rate of cooling must proceed very rapidly. In the prior art arrangements, the droplet solution surrounding the cell greatly reduced the rate of and uniformity of the cooling of the enclosed cells. However, by exploding the droplets 26, as accomplished in the present invention, the droplets 28, with their smaller cross-sectional dimensions, can be frozen much more rapidly and more uniformally. Hence, the means are provided for preserving viable microorganisms during freezing that heretofore would have not survived or at least had a very low survival rate.

At this point, the frozen droplets can be stored, and when needed, thawed according to the teachings of the above-mentioned U.S. Pat. No. 3,228,838 so as to have viable cells. Alternatively, the droplets can be dried using known sublimation techniques for biological materials, such as shown in U.S. Pat. No. 3,932,943 to Briggs et al. The frozen droplets 28, which are not cells or which do not contain cells, disappear either through thawing or drying. As with freezing, the smaller cross-sectional dimensions of the frozen droplets 28 provides for more rapid and uniform heat transfer during either thawing or drying by sublimation, as the case may be. If the cells are dried by sublimation, the residual crust of solute, which normally comprises salt and is formed around the cells, is substantially reduced so as to, in most cases, eliminate the need to remove the same prior to reconstituting the cells. Moreover, more uniform heat transfer can assist in minimizing overdrying of the cells.

If thawing is desired, the common practice is to submerge the frozen droplets 28 in a saline solution, as shown in the previously mentioned U.S. Pat. No. 3,228,838. If drying by sublimation is desired, the common procedure is to include conventional sublimation means 36 wherein the frozen droplets are subjected to a partial vacuum at a temperature such that the desired amount of ice can be sublimated from the cells. The frozen droplets not containing cells are entirely sublimated away. Thereafter, the cells are allowed to come to room temperature and pressure. When needed, the cells are reconstituted in a conventional manner to produce viable cells. One such arrangement suitable for sublimation means 36 is shown in the previously mentioned U.S. Pat. No. 3,932,943 and is incorporated herein.

Other microorganisms, such as bacteria, can be processed and preserved by the present invention. When the frozen droplets are to be thawed, the microorganisms can be suspended in an aqueous solution containing protective additives, such as glycerol, glucose, lactose, or polyvinyl pyrrolidone, or combinations of these, prior to freezing. Different protective additives are used in the prior art when the droplets are to be sublimated. Alternatively, the microorganisms can be suspended in standard liquid solutions employed in growing the microorganisms and then frozen in its own growing medium. In general, the solution will be an aqueous solution having a salt concentration therein, that, after sublimation, will leave a solute crust, primarily composed of salt. The use of the term "aqueous solution" is intended to cover all such possibilities, including a saline solution, whole blood or like solution, with and without protective additives.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. An apparatus for rapidly freezing microorganisms including means having at least one nozzle for producing droplets of an aqueous solution, having the microorganisms suspended therein, and means for freezing droplets containing microorganisms, the improvement comprising:
   electrode means positioned adjacent said nozzle substantially at the point of droplet formation;
   means for applying an electric potential difference between said nozzle and said electrode means of a strength great enough to break a droplet into a plurality of smaller droplets;
whereby said smaller droplets provide smaller cross-sectional dimensions relative to the droplets formed by said nozzle for more rapid cooling.

2. The apparatus of claim 1,
   means for sublimating a portion of the ice from the frozen microorganism to preserve the microorganism;
whereby the removal of a substantial portion of the aqueous solution from the microorganism prior to freezing provides for more rapid sublimation and reduces any solute buildup around the microorganism caused by the sublimation.

3. The apparatus of claim 1,
   the microorganisms comprising biological cells.

4. A method of preserving microorganisms including forming an aqueous solution of suspended microorganisms, forming droplets of the aqueous solution, the improvement comprising:

applying an electrical force to the droplets of a strength great enough to break a droplet into a plurality of smaller droplets;

freezing the smaller droplets.

5. The method of claim 4, sublimating a portion of the ice from the microorganism to preserve the microorganism;

reconstituting the microorganism without having to remove a crust of solute therefrom.

6. The method of claim 4, the microorganisms comprising biological cells.

* * * * *